United States Patent
Mayrand

(10) Patent No.: US 10,597,311 B2
(45) Date of Patent: Mar. 24, 2020

(54) SELF-CLEANING ULTRAVIOLET WASTEWATER DISINFECTION UNIT AND METHOD

(71) Applicant: BIOTURBINE SYSTEMS INC., Ville Saint-Laurent (CA)

(72) Inventor: Paul Mayrand, Ville Saint-Laurent (CA)

(73) Assignee: BIOTURBINE SYSTEMS INC., Ville Saint-Laurent (CA)

( * ) Notice: Subject to any disclaimer, the term of this patent is extended or adjusted under 35 U.S.C. 154(b) by 0 days.

(21) Appl. No.: 15/599,922

(22) Filed: May 19, 2017

(65) Prior Publication Data
US 2017/0253497 A1  Sep. 7, 2017

Related U.S. Application Data

(63) Continuation-in-part of application No. PCT/CA2015/051211, filed on Nov. 20, 2015.
(Continued)

(51) Int. Cl.
*A61L 2/10* (2006.01)
*B08B 7/02* (2006.01)
(Continued)

(52) U.S. Cl.
CPC .............. *C02F 1/32* (2013.01); *A61L 2/10* (2013.01); *B08B 3/10* (2013.01); *B08B 7/02* (2013.01);
(Continued)

(58) Field of Classification Search
None
See application file for complete search history.

(56) References Cited

U.S. PATENT DOCUMENTS 5,232,586 A * 8/1993 Malone .................. A01K 63/04
 210/150
5,393,419 A * 2/1995 Tiede ........................ A61L 2/10
 210/192

(Continued)

FOREIGN PATENT DOCUMENTS

CN 1341563 A 3/2002
CN 2503059 Y 7/2002

OTHER PUBLICATIONS

CN 1341563 A Machine Translation—Yu Jiande—Mar. 27, 2002 (Year: 2002).*

(Continued)

*Primary Examiner* — Bradley R Spies
(74) *Attorney, Agent, or Firm* — Borden Ladner Gervais LLP; Louis B. Allard

(57) ABSTRACT

A self-cleaning ultraviolet wastewater disinfection unit and method are provided. The disinfection unit has a wastewater treatment chamber comprising a UV lamp for treating/disinfecting the wastewater. A plurality of pieces of media may be positioned in the treatment chamber. When wastewater is present in the chamber, gas is injected into the wastewater through a gas inlet conduit. The gas agitates the pieces of media in the wastewater to cause the pieces of media to rub against the UV lamp unit to remove matter that has accumulated on the UV lamp unit. The removal of accumulated matter on the UV lamp and other surfaces in the chamber may improve the efficiency and effectiveness of the disinfecting unit. Furthermore, the cleaning operation may be performed automatically at scheduled periods to increase the time between major cleanings of the unit.

17 Claims, 14 Drawing Sheets

Related U.S. Application Data

(60) Provisional application No. 62/082,838, filed on Nov. 21, 2014.

(51) Int. Cl.
  *C02F 1/00* (2006.01)
  *C02F 1/32* (2006.01)
  *C02F 1/74* (2006.01)
  *B08B 3/10* (2006.01)

(52) U.S. Cl.
  CPC ............... *C02F 1/325* (2013.01); *C02F 1/00* (2013.01); *C02F 1/74* (2013.01); *C02F 2201/324* (2013.01); *C02F 2201/3223* (2013.01); *C02F 2201/3224* (2013.01); *C02F 2201/3228* (2013.01); *C02F 2303/04* (2013.01)

(56) References Cited

U.S. PATENT DOCUMENTS

| | | | | |
|---|---|---|---|---|
| 7,049,615 B1* | 5/2006 | Browne | ............ | C02F 1/002 250/504 R |
| 2003/0080054 A1* | 5/2003 | Chuang | ............ | C02F 3/087 210/616 |
| 2005/0252866 A1* | 11/2005 | Beckinghausen | ....... | C02F 1/283 210/748.08 |
| 2006/0006104 A1* | 1/2006 | Cary | ............ | C02F 1/006 210/167.01 |
| 2007/0248488 A1* | 10/2007 | Denkewicz, Jr. | ....... | C02F 1/325 422/24 |
| 2008/0283467 A1* | 11/2008 | Nguyen | ............ | B63B 35/00 210/600 |
| 2013/0020500 A1* | 1/2013 | McKinney | ............ | A61L 2/10 250/436 |
| 2013/0228527 A1* | 9/2013 | Crasti | ............ | C02F 1/004 210/747.2 |

OTHER PUBLICATIONS

International Patent Application No. of PCT/CA2015/051211, International Preliminary Report on Patentability dated Jun. 1, 2017.
International Patent Application No. PCT/CA2015/051211, International Search Report and Written Opinion dated Jan. 28, 2016.

\* cited by examiner

SELF-CLEANING ULTRAVIOLET WASTEWATER DISINFECTION UNIT AND METHOD

FIELD

The present disclosure relates generally to the disinfection of wastewater, and more particularly to the removal of an accumulated biofilm or other matter from an inner surface of water disinfection equipment.

BACKGROUND

Ultraviolet (UV) water disinfection systems utilize UV light to kill bacteria in the water. The effectiveness of such systems depends on the water being exposed to a sufficient amount of UV light. If the water being treated is not exposed to a sufficient amount or intensity of UV light for a sufficient time period, an unacceptable level of bacteria may remain in the water, thereby posing a potential health risk.

Over time, biofilms or other organic or inorganic coatings may grow or accumulate on the inner surfaces of a water disinfection system. In general terms, a biofilm is a thin layer of microorganisms that has adhered to the surface of a structure. Biofilms can result from bacterial, fungal, or algal growth.

In the case of a UV disinfection system, such coatings can accumulate on a surface of a UV light source in the system. Such coatings can begin to block some of the light emitted from the UV light source from reaching the water being treated, thereby potentially reducing the effectiveness of the UV disinfection system. As a result, UV disinfection equipment can often require regular periodic cleanings to remove biofilms or other matter that has accumulated on the surface of the UV light source. However, the process of cleaning such equipment is often tedious, difficult or time consuming. Furthermore, periodic cleanings are often neglected or forgotten.

SUMMARY

According to one aspect, the present disclosure is directed to a wastewater disinfection unit comprising a treatment chamber to receive wastewater; an ultraviolet (UV) lamp unit located within the treatment chamber; a gas inlet conduit in fluid communication with the treatment chamber; and pieces of media positioned within the treatment chamber, such that when wastewater is present in the chamber and gas is injected into the wastewater through the gas inlet conduit, the gas agitates the pieces of media in the wastewater to cause the pieces of media to rub against the UV lamp unit to remove matter that has accumulated on the UV lamp unit.

In an example embodiment, the wastewater disinfection unit further comprises a wastewater inlet through which the wastewater to be disinfected enters the wastewater disinfection unit; and a wastewater outlet through which disinfected wastewater exits the wastewater disinfection unit. The wastewater inlet and the wastewater outlet are each positioned at a respective height, and the height of the wastewater inlet and the height of the wastewater outlet are set to maintain a wastewater level in the treatment chamber above the UV lamp unit.

In an example embodiment, the density of the pieces of media is within the range of approximately 1.05 to 1.15 g/cm$^3$.

In an example embodiment, the pieces of media consist substantially of plastic.

In an example embodiment, the wastewater disinfection unit comprises at least two gas inlet conduits in fluid communication with the treatment chamber, wherein the gas inlet conduits are oriented within the treatment chamber to induce a vortex effect in the wastewater when gas is injected into the wastewater through the gas inlet conduits.

In an example embodiment, the wastewater disinfection unit comprises a strainer disposed within the treatment chamber for preventing pieces of media from flowing out of the treatment chamber.

In an example embodiment, the gas inlet conduit is positioned below the strainer.

In an example embodiment, the wastewater disinfection unit comprises an input section for receiving wastewater into the treatment chamber; and a filter for preventing pieces of media from exiting the treatment chamber through the input section.

In an example embodiment, the wastewater disinfection unit comprises a gas exhaust conduit in fluid communication with the treatment chamber for allowing gas to leave the treatment chamber as gas is injected into the wastewater through the gas inlet conduit.

In an example embodiment, the wastewater disinfection unit comprises an exhaust valve positioned along the gas exhaust conduit that may be selectively closed when no gas is to be injected into the wastewater through the gas inlet conduit to prevent the flow of wastewater from the treatment chamber through the gas exhaust conduit.

In an example embodiment, the wastewater disinfection unit comprises a wastewater supply conduit for receiving wastewater into the treatment chamber; and a supply valve positioned along the wastewater supply conduit that may be selectively closed when gas is going to be injected into the wastewater to prevent backflow of wastewater or gas from the treatment chamber into the wastewater supply conduit.

In an example embodiment, the wastewater disinfection comprises a dosing mechanism in fluid communication with the treatment chamber for selectively providing a dose of cleaning substance into the treatment chamber.

According to another aspect, the present disclosure is directed to a method of removing matter that has accumulated on a surface located within a wastewater treatment chamber of a wastewater disinfection unit. The method may comprise providing pieces of media within the treatment chamber; providing wastewater within the treatment chamber; and injecting gas into the wastewater in the treatment chamber to agitate the pieces of media in the wastewater to cause the pieces of media to rub against the surface within the treatment chamber to remove the accumulated matter on the surface.

In an example embodiment, the surface includes an ultraviolet (UV) lamp unit.

In an example embodiment, the pieces of media have a density higher than water.

In an example embodiment, the injecting of gas into the wastewater involves directing gas within the wastewater to induce a vortex effect in the wastewater.

In an example embodiment, the method comprises injecting gas into the wastewater from at least two different locations within the treatment chamber.

In an example embodiment, the method comprises selectively opening an exhaust valve positioned along a gas exhaust conduit in fluid communication with the treatment chamber to exhaust gas from the treatment chamber during the injecting gas into the wastewater.

In an example embodiment, the method comprises selectively closing a supply valve positioned along a wastewater supply conduit in fluid communication with the treatment chamber to prevent backflow of wastewater or gas from the treatment chamber into the wastewater supply conduit.

In an example embodiment, the method comprises selectively providing a dose of cleaning substance into the treatment chamber.

BRIEF DESCRIPTION OF THE DRAWINGS

Embodiments of the present disclosure will now be described, by way of example only, with reference to the attached Figures.

DETAILED DESCRIPTION

Generally, the present disclosure provides an ultraviolet (UV) wastewater disinfection unit and a method of preventing or removing the formation or accumulation of matter, such as a biofilm, within the UV wastewater disinfection unit. The removal of such films can maintain water contact surfaces in the UV wastewater disinfection unit in a relatively clean state and result in improved efficiency and effectiveness of the UV disinfecting unit.

The wastewater to be treated enters a treatment chamber equipped with a UV lamp unit that irradiates the wastewater and the bacteria present therein. The bacteria are killed by the UV light. The treatment chamber is equipped with an air inlet conduit connected to an air source and comprises several pieces of media that, upon air being pushed into the treatment chamber by the air source, move within the treatment chamber and rub or brush up against the UV lamp unit as well as against the surface of other components of the disinfection unit within the chamber, such as the inner wall surface of the treatment chamber. The brushing or rubbing movement (e.g. friction) of the media against the UV lamp unit and against the inner wall surface of the treatment chamber mitigates the accumulation of a biofilm or other organic or inorganic coating on the UV lamp unit and on the inner wall surface. The turbulence in the wastewater created by air flowing in the wastewater also mitigates the accumulation of such biofilms. This allows for prolonged use of the UV disinfection unit without the need for a major cleaning of the treatment chamber and its components at short time intervals.

Figure 1:
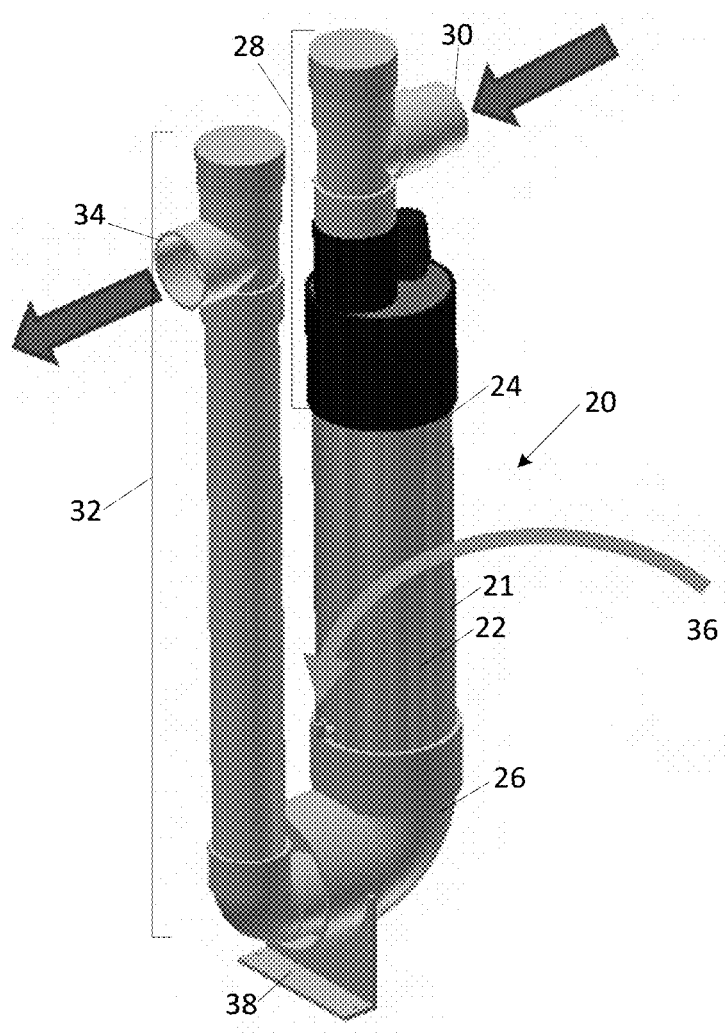
FIG. 1 shows a perspective view of an embodiment of a UV disinfection unit in accordance with the present disclosure.

FIG. 1 shows a perspective view of an embodiment of a UV disinfection unit 20 in accordance with the present disclosure. The UV disinfection unit 20 has a treatment chamber 22 defined at least partly by chamber wall 21. Chamber 22 has an input section 24 and an output section 26. In the present embodiment, the input section 24 has connected thereto a connector assembly 28 that connects the treatment chamber 22 to a source of wastewater. The connector assembly 28 has a wastewater inlet 30. As an example, the source of wastewater for the UV disinfection unit 20 may include the output of a residential or multi-dwelling wastewater treatment system that separates solids from liquids and partially treats the liquid portion of the wastewater using rotating biological contactors.

Also, in the present embodiment, the output section 26 is connected to a wastewater outlet section 32 that outputs disinfected wastewater at a wastewater outlet 34. Additionally, an air inlet conduit 36 allows for an air source (not shown) or, more generally, a gas source, to be connected to the treatment chamber 22 to periodically inject air into the treatment chamber 22. The air inlet conduit 36 can be connected with any suitable type of piping or tubing to an air source. The air source can be an air pump configured to pump air into the air inlet conduit at pre-determined time intervals such as, for example, once a day for a 5 to 10 minute period. In some embodiments, a cleaning operation may be conducted two or more times daily. Furthermore, the UV disinfection unit 20 may be programmable to perform one or more cleaning operations automatically, meaning without requiring any human intervention. A support structure 38 allows the UV disinfection unit to be supported by an underlying surface (not shown). The arrows indicate the direction of flow of the wastewater into the wastewater inlet 30 and out to the wastewater outlet 34.

Although various embodiments are described herein as using air to agitate wastewater in the chamber to cause movement of the pieces of media, other types of gases may be used.

Figure 2:
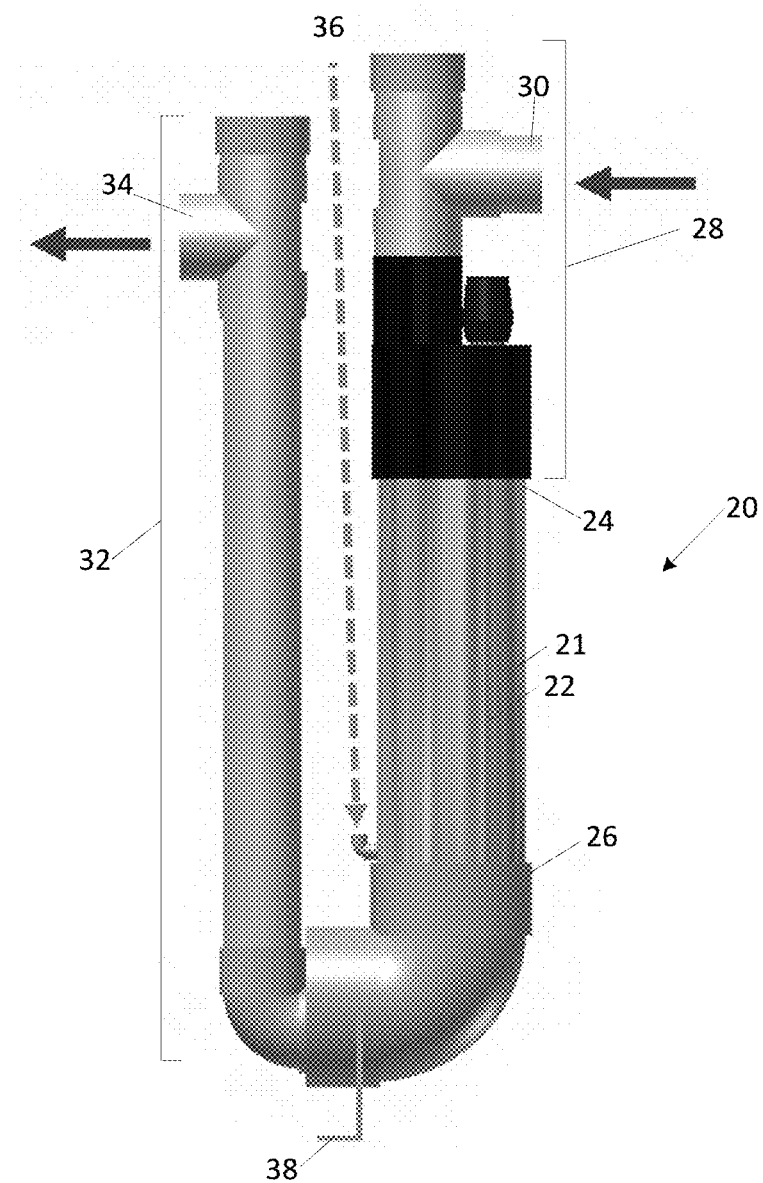
FIG. 2 shows a side view of the UV disinfection unit of FIG. 1.

FIG. 2 shows a side view of the UV disinfection unit 20 shown in FIG. 1. As shown in FIG. 2, the wastewater outlet 34 may be positioned lower than the wastewater inlet 30. This allows the wastewater to flow from the wastewater inlet 30 to the wastewater outlet 34 by gravity. Also shown in FIG. 2, the treatment chamber 22 has a diameter larger than that of the wastewater input 30 and larger than that of the wastewater outlet section 32. This allows for wastewater to be slowed down in the treatment chamber 22. That is, the wastewater flows at a slower speed in the treatment chamber 22 than in the wastewater inlet 30 and the wastewater outlet section 32. This allows for the wastewater in the treatment chamber 22 to be exposed to UV irradiation for a longer time period than would be possible if the diameter of the treatment chamber 22 were the same as that of the wastewater inlet 30 and of the wastewater outlet section 32. This, in turn, allows for greater disinfection of the wastewater.

Figure 3:
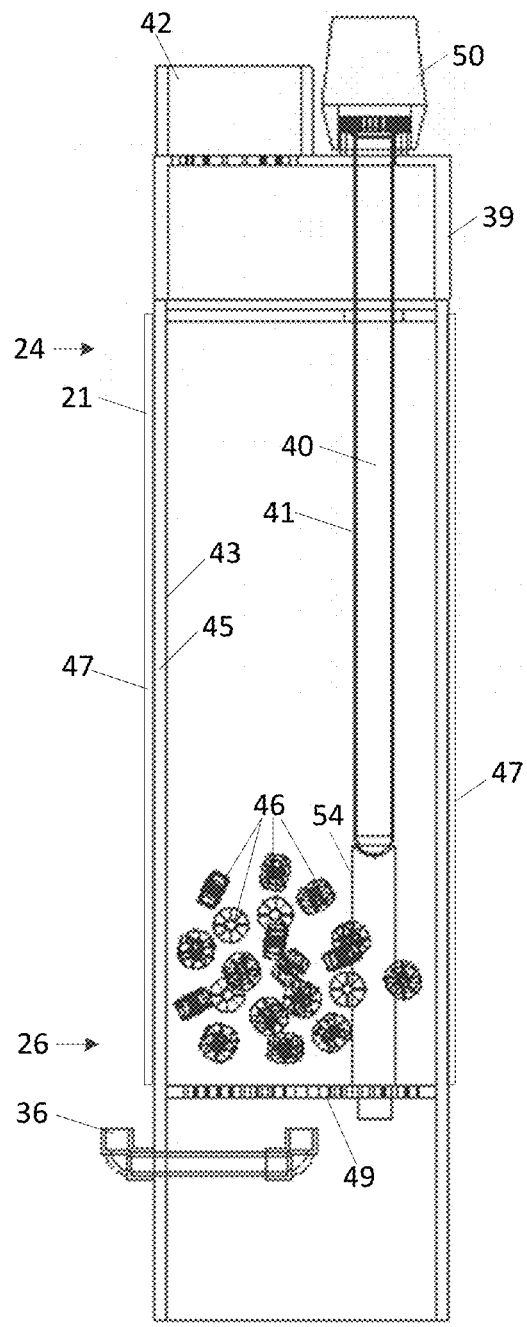
FIG. 3 shows a see-through, side view of the treatment chamber and of the head adaptor of the UV disinfection unit of FIG. 1.

FIG. 3 shows a see-through, side view of the treatment chamber 22 and of a head adaptor 39, which is part of the connector assembly 28 (shown at FIGS. 1 and 2). A UV lamp unit 40 is connected to the head adaptor 39 and extends into the treatment chamber 22. The UV lamp unit 40 includes a UV lamp (not shown) positioned within a sleeve 41, which may be made of glass or other suitable material. UV lamp unit 40 may comprise an electrical ballast 50, which may be located at head adaptor 39, for limiting the electrical current in the UV lamp. Wastewater enters the head adaptor 39 through an opening 42 and flows into the treatment chamber.

Comprised in the treatment chamber 22 are several pieces of media 46. These pieces of media 46 are pushed upwards in the treatment chamber 22 upon air being injected in the treatment chamber 22 through the air inlet conduit 36. Upon the air supply to the treatment chamber 22 being cut-off, the pieces of media fall towards the bottom of the treatment chamber 22. Upon movement of the pieces of media within the treatment chamber, the pieces of media rub up against the lamp sleeve 41 as well as against the surface of other components of disinfection unit 20 within chamber 22, including the inner wall surface 43 of chamber 22. The brushing or rubbing movement of the pieces of media against the surfaces of components within treatment chamber 22 has a cleaning effect on these surfaces. For example, the rubbing may mitigate the accumulation of a biofilm or other matter on the surfaces within the chamber. A growth or accumulation of a biofilm or other substance on the UV lamp unit may obstruct some of the light emitted by the UV lamp from entering the chamber, possibly reducing the effectiveness of the UV lamp to kill bacteria in the wastewater. The turbulence in the wastewater created by air flowing in the wastewater may also mitigate the accumulation of such biofilms or other matter. This may allow for prolonged use of the disinfection unit without the need for a significant cleaning of the treatment chamber and its components at short time intervals.

In some embodiments, the pieces of media 46 have a density slightly higher than that of water (for example in the range of approximately 1.05 to 1.15 g/cm$^3$) so that they sink in the wastewater in treatment chamber 22 when air is not being injected into chamber 22 but are easily propelled upwardly in chamber 22 by air that is forced into chamber 22 during cleaning. The pieces of media 46 may have a size of 10 mm or less, may have a mass of 5 grams or less per piece, and may be me fabricated substantially of or comprise plastic, such as UV stabilized polyethylene. In an embodiment, one or more pieces of media 46 may have a diameter of approximately 10 mm and a thickness of approximately 7 mm. However, additionally or alternatively, the pieces of media 46 may have other suitable dimensions without departing from the scope of the present disclosure. Further, the pieces of media 46 are not required to all have the same dimensions. Furthermore, pieces of media 46 may have an outer surface that is adapted for rubbing or scrubbing action against sleeve 41 and inner surfaces of chamber 22, including chamber wall 21, without causing scratching or other damage to the surfaces.

Furthermore, the volume occupied by the pieces of media 46 in the treatment chamber in relation to the total volume of the treatment chamber may be referred to as a chamber filling ratio. For example, a 20% filling ratio means that the pieces of media occupy 20% of the volume of the treatment chamber. In some embodiments, the filling ratio may be in one or more of the approximate ranges of 10% to 25%, 20 to 25%, 10 to 15%, or any other suitable range. The filling ratio may be selected to achieve a suitable amount or rate of cleaning in the treatment chamber. A filling ratio that is too high or too low results in less effective or efficient cleaning of the chamber. Further, if the filling ratio is too high, the pieces of media can become prone to having a biofilm formed thereon, which can reduce the flow of water in the treatment chamber. It is to be appreciated that the above features relating to media 46 are provided as examples only and are not meant to be limiting.

In some embodiments, the treatment chamber wall 21 can include of a UV transparent material 45 such as a clear PVC material and can be surrounded by a UV reflective portion or sleeve 47, which can be made of, for example, polished stainless steel. In such embodiments, UV light propagates from the UV lamp unit 40 through the wastewater, traverses the UV transparent PVC material 45, and reflects off the UV reflective sleeve 47 back into the wastewater. This allows additional exposure of wastewater to UV irradiation, which increases the killing of bacteria.

The treatment chamber 22 may also include a strainer 49 that allows wastewater to flow therethrough but that keeps the pieces of media within the treatment chamber 22.

Figure 4:
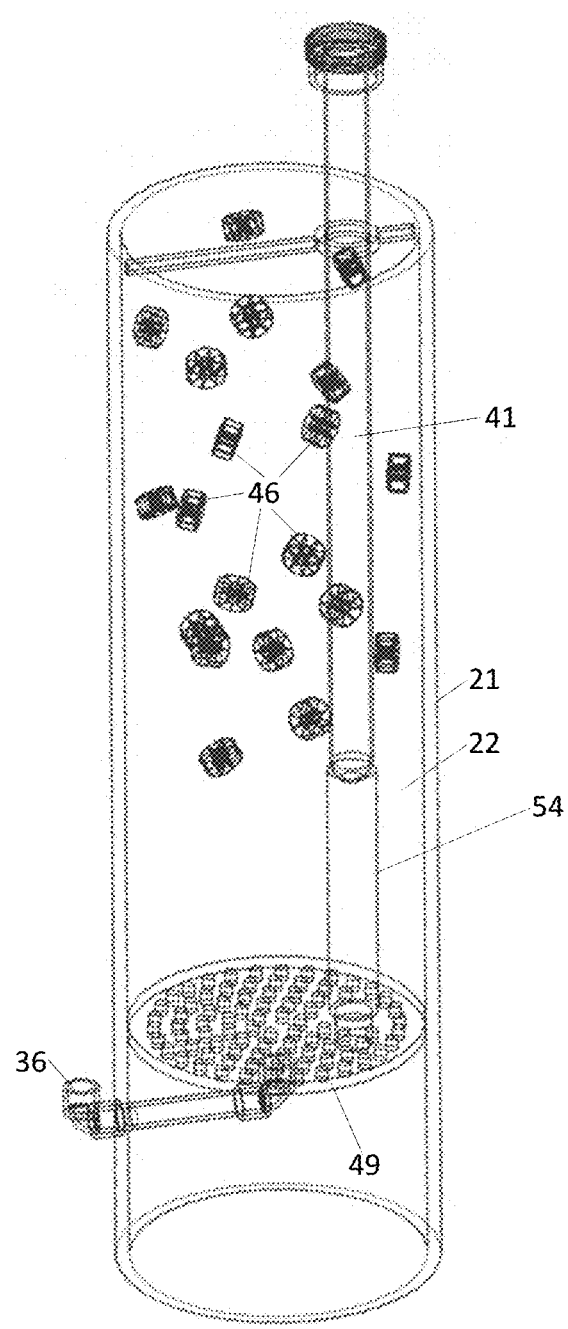
FIG. 4 shows a see-through, perspective view of the treatment chamber of the UV disinfection unit of FIG. 1.

FIG. 4 shows a perspective, see-through view of the treatment chamber 22 with pieces of media 46 being pushed upwards, within the wastewater, upon air being injected into the treatment chamber 22 through the air inlet conduit 36. The UV reflective sleeve 47 of FIG. 3 is not shown in FIG. 4. With reference to FIGS. 3 and 4, strainer 49 may be disposed at or near output section 26 of treatment chamber 22 to prevent the pieces of media 46 from flowing out of the chamber through wastewater outlet section 32. Furthermore, although strainer 49 is shown as defining a plurality of holes therethrough, other types of straining structures may be used. In addition, some embodiments may include a support for stabilizing lamp sleeve 41 within chamber 22. For instance, in the embodiment shown in FIGS. 3 and 4, a UV sleeve support 54 is positioned between the free end of sleeve 41 and strainer 49 for retaining lamp sleeve 41 in position.

In the embodiment shown at FIGS. 3 and 4, air injected into the air inlet conduit 36 exits the air input conduit in the treatment chamber, below the strainer 49. This need not be the case; the air inlet conduit 36 may configured differently to have air exit therefrom above the strainer without departing from the scope of the present disclosure. Further, more than one air inlet conduit 36 can be used to provide air into the treatment chamber. For example, two air inlet conduits may be arranged to generate a wastewater vortex within the treatment chamber. Air may exit treatment chamber 22 through wastewater inlet 30.

Figure 5:
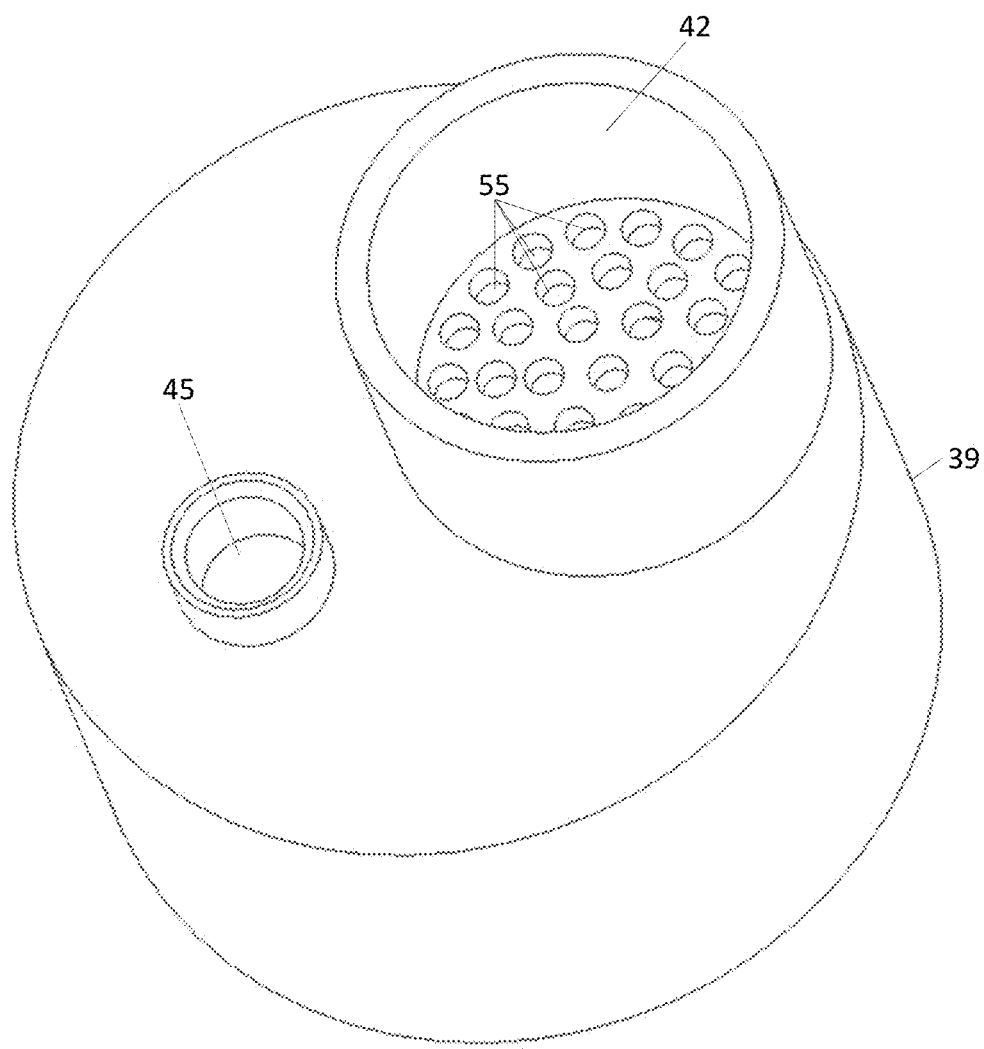
FIG. 5 shows a perspective view of the head adaptor of the UV disinfection unit of FIG. 1.

FIG. 5 shows a perspective view of the head adaptor 39 in one embodiment, which defines an opening 42 through which wastewater enters treatment chamber 22. The head adaptor 39 may further comprise a filter structure at opening 42 for allowing the wastewater to enter the treatment chamber and to prevent the pieces of media from exiting the treatment chamber, such as a plurality of apertures 55 or some other filtering structure. Furthermore, the head adaptor may define a through-hole 45 through which the UV lamp unit can be inserted into the treatment chamber.

In the embodiments shown in FIGS. 1 to 5, the UV lamp unit is not centrally located within the treatment chamber. This need not be the case. The head adapter through which wastewater enters the treatment chamber may be configured to have a through-hole centrally located to receive and position the UV lamp unit in the center of the treatment chamber.

Figure 6:
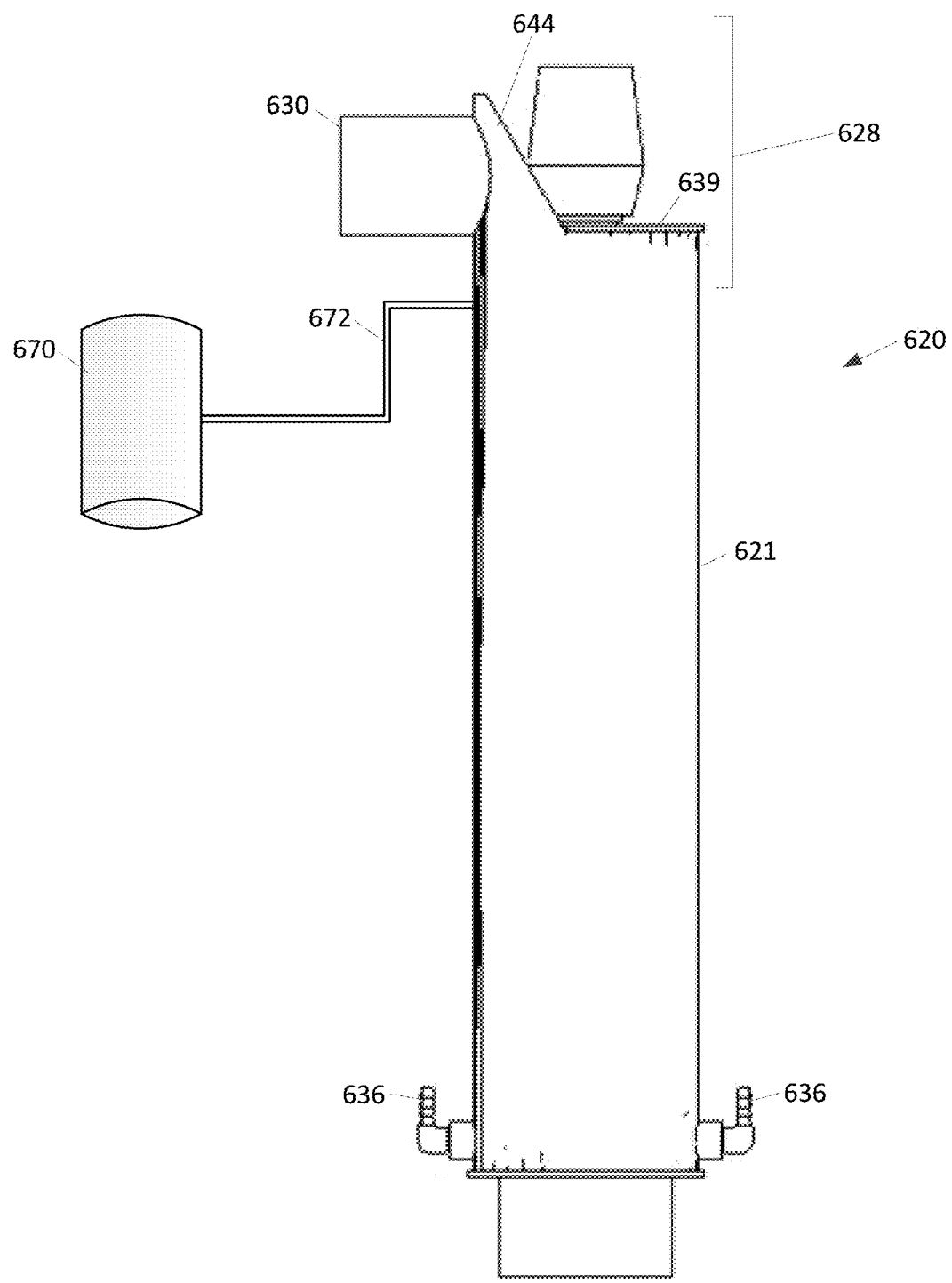
FIG. 6 shows a side view of another embodiment of a UV disinfection unit according to the present disclosure.
Figure 7:
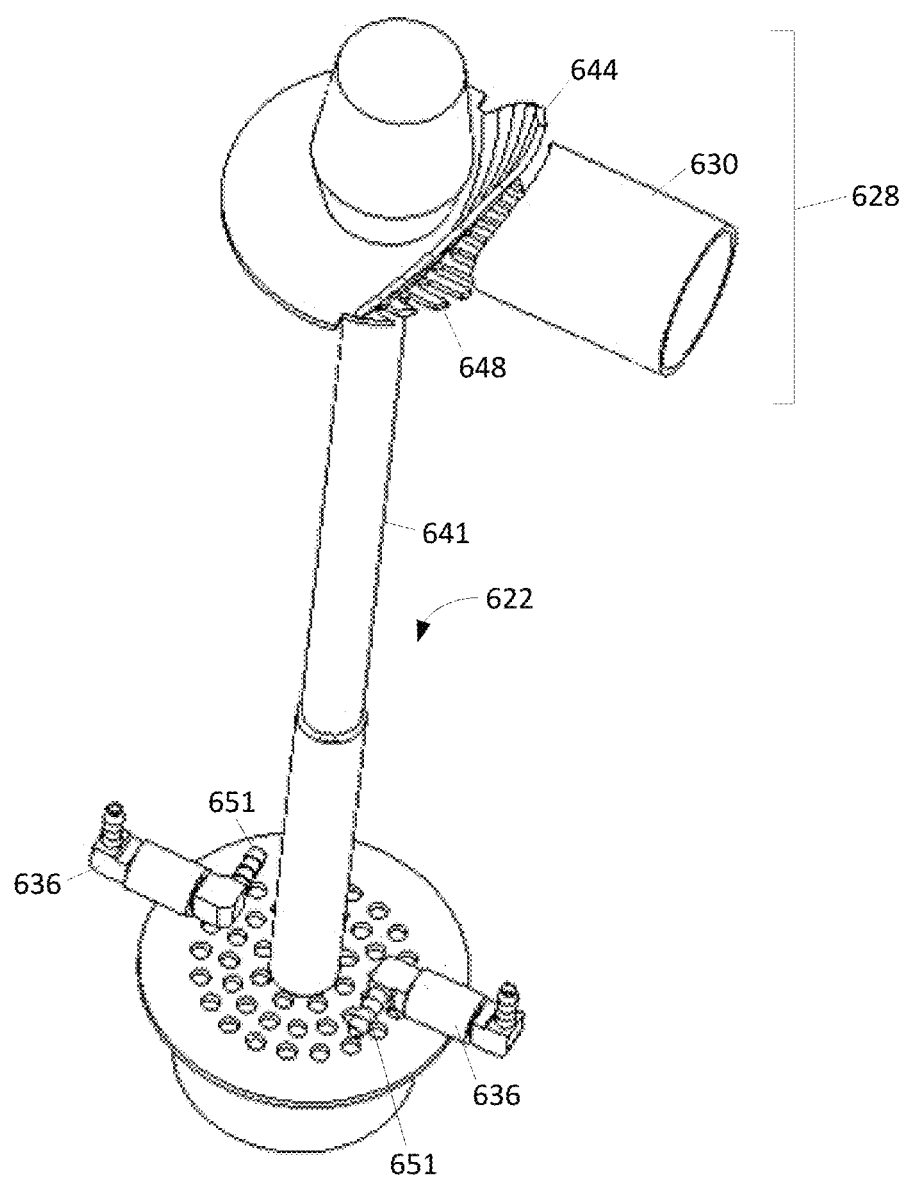
FIG. 7 shows an upper perspective view of the embodiment of FIG. 6 with the treatment chamber wall removed.

FIGS. 6 and 7 show another embodiment of a UV disinfection unit according to the present disclosure. FIG. 6 shows a side view of UV disinfection unit 620 having a connector assembly 628 and head adapter 639 that differs from those of the previously described example embodiments. Wastewater inlet 630 interfaces with head adapter 639 through an angled conduit 644. FIG. 7 shows an upper perspective view of this example embodiment with treatment chamber wall 621 and portions of angled conduit 644 removed to show inner components of the UV disinfection unit 620. Part of angled conduit 644 may have a scalloped shape. Furthermore, connector assembly 628 may include a filter structure, such as comb or slotted filter 648, for preventing the pieces of media 46 (not shown in FIG. 6 or 7) from exiting treatment chamber 622 towards wastewater inlet 630. The inner cross sectional area of angled conduit 644 may be similar or the same as an inner cross sectional area of wastewater inlet 630.

In addition, UV disinfection unit 620 may comprise two air inlet conduits 636. The inner ends 651 of the air inlet conduits 636 may be oriented to induce a vortex effect in the water within treatment chamber 622 when air is forced through air inlet conduits 636. In the embodiment shown in FIG. 7, inner ends 651 of air inlet conduits 636 are directed in opposite directions for inducing a vortex in the wastewater. A vortex effect may serve to increase the rubbing action of the pieces of media 46 on sleeve 641 and on inner surfaces of treatment chamber 622, including the inner surface of chamber wall 621.

Furthermore, some embodiments may include a mechanism for providing a cleaning substance into the wastewater in treatment chamber 22 to provide further cleaning of the chamber. The cleaning of treatment chamber 22 and other disinfection equipment using a cleaning substance may be useful in removing or killing bacteria in the equipment, such as coliform bacteria. FIG. 6 is an example embodiment comprising a dosing pump 670 in fluid communication with chamber 22 through dosing conduit 672. Dosing pump 670 may be adapted or configured to dispense or inject a cleaning substance, such as a soap or liquid chlorine solution, into treatment chamber 22. The cleaning substance may be injected during some or all cleaning operations. For example, the cleaning substance may be injected daily, weekly, or on any other suitable schedule. Furthermore, the dosing pump 670 may be programmed to perform the dosing of cleaning substance automatically, meaning without any human intervention. In some embodiments, the combination of the rubbing action of the pieces of media 46 and the cleaning substance may enhance the overall cleaning effect within the chamber. The amount of cleaning substance injected at a given time may depend on the size of treatment chamber 22 or the concentration of the cleaning substance. As a mere example, 30 to 50 ml of soap or chlorine may be sufficient for a 4 L treatment chamber. Dosing pump 670 may be provided with a supply of cleaning substance, for example in a reservoir (not shown), to allow for multiple injections without refilling. For example, the supply of cleaning substance may be able to last for several months.

Figure 8:
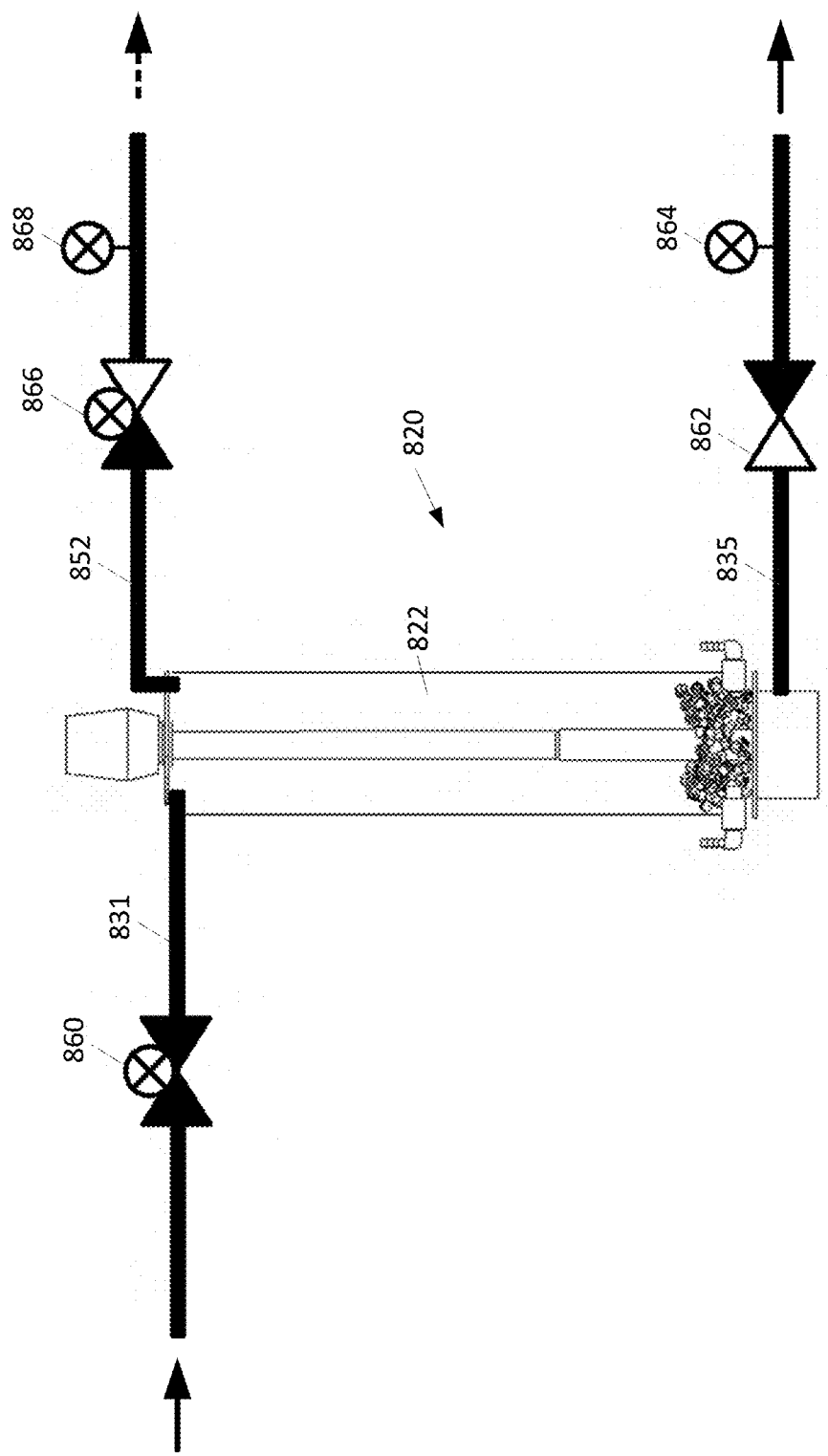
FIG. 8 shows a see-through, side view of another embodiment comprising a UV disinfection unit according to the present disclosure.

FIG. 8 shows yet another example embodiment comprising a UV disinfection unit 820 according to the present disclosure. This embodiment may be used in combination with a pressurized wastewater supply. The UV disinfection unit 820 comprises wastewater supply conduit 831 and wastewater exit conduit 835. This embodiment further includes an air exhaust conduit 852 in fluid communication with treatment chamber 822 for allowing air or other gas that is forced into chamber 822 during a cleaning operation to exit chamber 822. The embodiment may also comprise one or more valves that may be opened or closed depending on whether a cleaning operation is to be performed. The example embodiment comprises a supply valve 860, an exit valve 862, and an exhaust valve 866. Supply valve 860 and exhaust valve 866 may be solenoid valves, whereas exit valve 862 may be a check valve. During normal operation, meaning when a cleaning operation is not in progress, supply valve 860 may be open to allow wastewater to flow into treatment chamber 822 while exhaust valve 866 may be closed to prevent wastewater from flowing out of chamber 822 through air exhaust conduit 852. In contrast, when a cleaning operation is to be performed in treatment chamber 822, exhaust valve 866 may be opened and supply valve 860 may be closed to prevent the backflow of wastewater or gas from chamber 22 into wastewater supply conduit 831. Additionally or alternatively, supply valve 860 may be closed to prevent the flow of wastewater into treatment chamber 22 during a cleaning operation. This may be appropriate, for example, when the wastewater supply is pressurized.

Furthermore, an exhaust flow monitoring device 868 may be located downstream from exhaust valve 866 to detect or monitor wastewater flow out of treatment chamber 822 through air exhaust conduit 852. For example, if the amount of wastewater flowing through air exhaust conduit 852 exceeds a threshold, an alarm may be triggered or other action may be taken, for example stopping the cleaning operation. In addition, an exit flow monitoring device 864 may be located downstream from exit valve 862 for detecting water flow in wastewater exit conduit 835.

Figure 9:
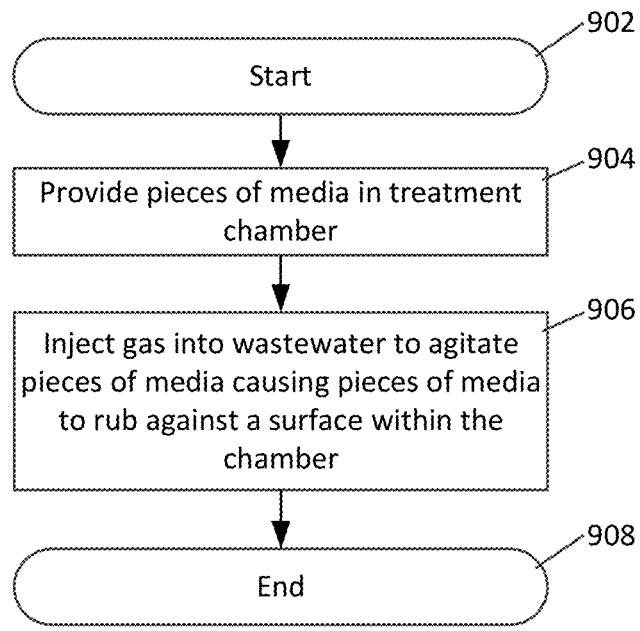
FIG. 9 shows a flow diagram comprising steps of a process according to the present disclosure.

The present disclosure also contemplates processes for cleaning wastewater disinfection equipment. FIG. 9 is a flow diagram showing steps of a process according to the present disclosure. The process begins at block 902 and proceeds to block 904, where pieces of media are provided in the treatment chamber of a wastewater disinfection unit. Wastewater may already be present in the treatment chamber or may be added. The process then proceeds to block 906, where gas is injected into the wastewater in the treatment chamber to agitate the pieces of media in the wastewater. The agitation causes the pieces of media to rub against the surface of a component within the treatment chamber, such as the lamp sleeve, or chamber wall. The rubbing may result in the pieces of media removing accumulated matter from the one or more the surfaces in the treatment chamber. The rubbing action may reduce or prevent the formation or buildup of biofilm or other matter. In addition, the turbulence in the wastewater caused by the agitation may also mitigate the accumulation of biofilms or other matter since the moving water may also have a rubbing effect on the surfaces in the chamber. The process then proceeds to block 908 where the process ends.

Figure 10:
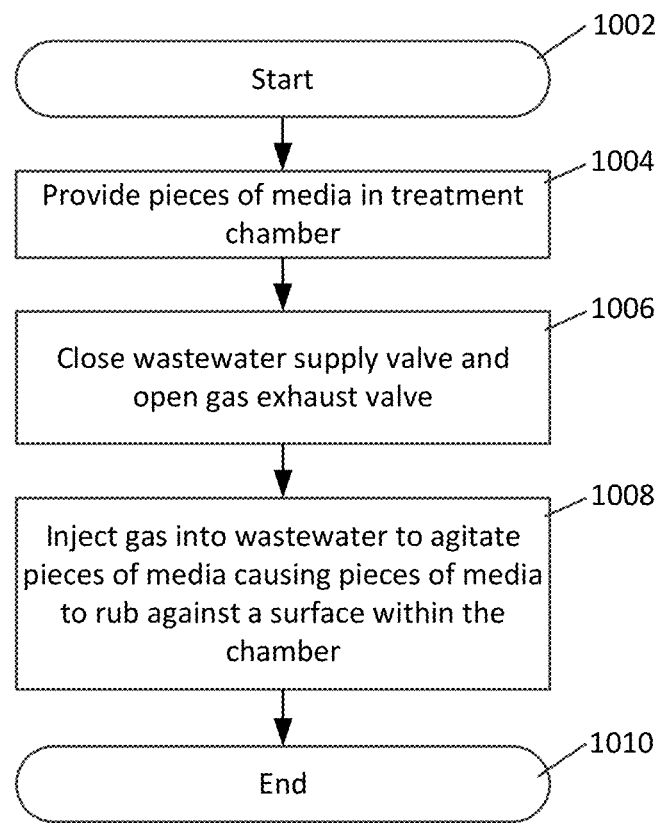
FIG. 10 shows a flow diagram comprising steps of another process according to the present disclosure.

FIG. 10 is a flow diagram showing steps of another process according to the present disclosure. The process begins at block 1002 and proceeds to block 1004, where pieces of media are provided in the treatment chamber of a wastewater disinfection unit. Again, it is assumed that wastewater is present in the treatment chamber or is added thereto. The process then proceeds to block 1006, where a supply valve in a wastewater supply conduit to the disinfection unit is closed and an exhaust valve in an air exhaust conduit leaving the disinfection unit is opened. The process then proceeds to block 1008, where gas is injected into the wastewater in the treatment chamber to agitate the pieces of media in the wastewater. Again, the movement of the pieces of media within the treatment chamber may act to rub and clean the surface of one or more components within the chamber, as previously described. Furthermore, as gas is forced into the treatment chamber, some gas will be forced out of the chamber and into the gas exhaust conduit. The process then proceeds to block 1010 where the process ends.

Although the above example embodiments relate to an ultraviolet disinfecting unit and method for disinfecting wastewater, the present disclosure also applies to an ultraviolet disinfecting unit and method for disinfecting drinking water. The following describes such an embodiment.

Figure 11:
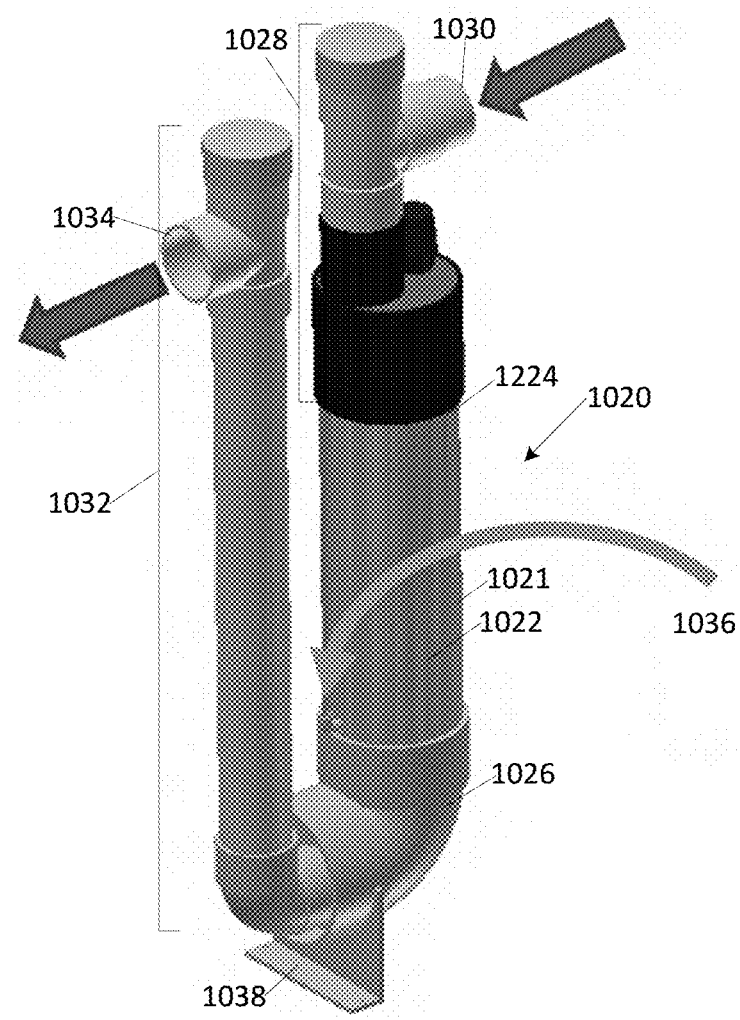
FIG. 11 shows a perspective view of another embodiment of a UV disinfection unit in accordance with the present disclosure.

FIG. 11 shows a perspective view of another embodiment of a UV disinfection unit 1020 in accordance with the present disclosure. The UV disinfection unit 1020 has a treatment chamber 1022 defined at least partly by chamber wall 1021. Chamber 1022 has an input section 1024 and an output section 1026. In the present embodiment, the input section 1024 has connected thereto a connector assembly 1028 that connects the treatment chamber 1022 to a source of drinking water. Such sources of drinking water may include, for example, water obtained from a well or from an open body of water. The connector assembly 1028 has a drinking water inlet 1030. The UV disinfection unit 1020 works the same way with respect to drinking water as does the UV disinfection units 20 and 820 described above in relation to wastewater treatment.

In some embodiments, the UV disinfection unit 1020 may be connected to a dosing pump, such as dosing pump 670 shown at FIG. 6, to inject a cleaning substance in the treatment chamber of the UV disinfection unit 1020. As will be understood by the skilled worker, in order to avoid the drinking water to contain unsuitable amounts of the cleaning substance, a purge of the treatment chamber may be warranted prior to having anyone ingest the drinking water treated by the US disinfection unit 1020.

The example methods related to wastewater treatment and described in relation to FIGS. 9 and 10 are also applicable to the treatment of drinking water.

The embodiments described above have water propagating through the treatment chamber from top to bottom (downward flow) and the pieces of media moving upwards, against the flow of the water being treated, when subjected to an air flow originating at a lower portion of the treatment chamber. The inventor has discovered that this need not be the case and that inversing the flow of water through the treatment chamber also produces effective cleaning of the UV lamp unit.

Figure 12:
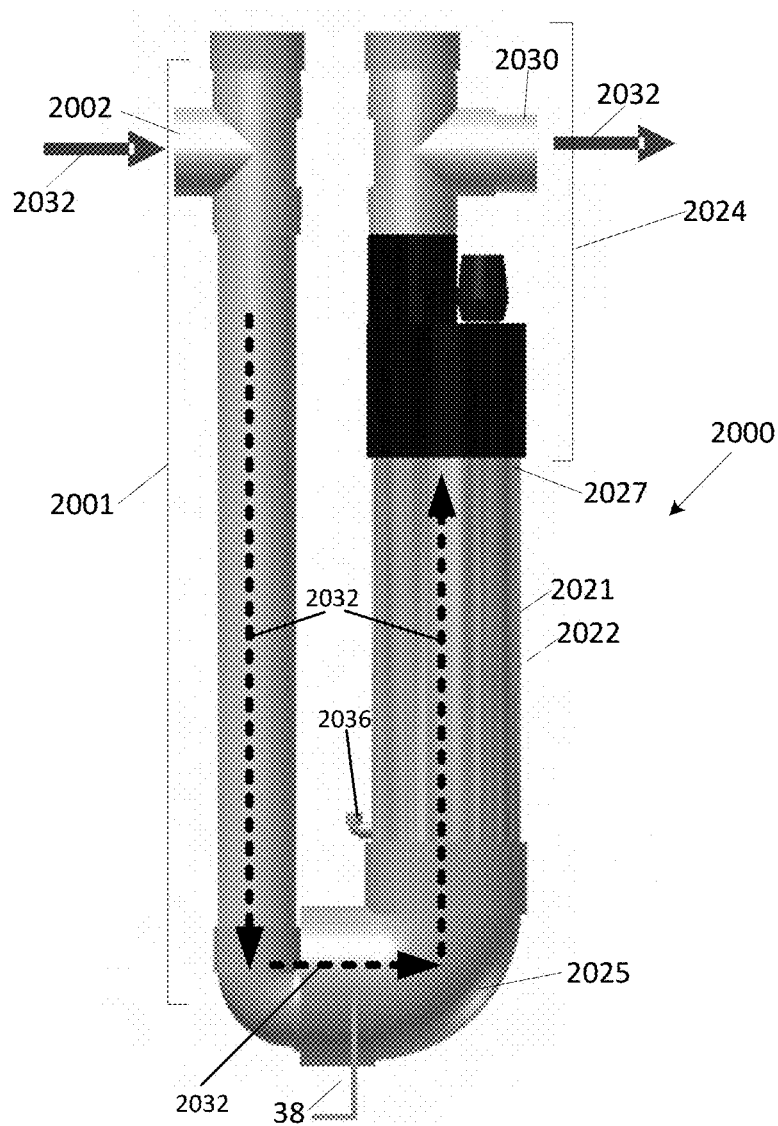
FIG. 12 shows a side view of an embodiment of a UV disinfection unit in accordance with the present disclosure.

FIG. 12 shows a side view of an embodiment of a UV disinfection unit 2000 in accordance with the present disclosure where, in this embodiment, the wastewater to be disinfected flows upwards in the treatment chamber rather than downwards.

The UV disinfection unit 2000 comprises the treatment chamber 2022 defined at least partly by chamber wall 2021. The treatment chamber 2022 has an input section 2025 through which wastewater to be disinfected enters the treatment chamber 2022 (at a bottom portion of the treatment chamber) and an output section 2027 through which disinfected wastewater exits the treatment chamber 2022 (at a top portion of the treatment chamber). In the present embodiment, the input section 2025 is connected (fluidly connected) to a wastewater inlet section 2001 that connects the source of wastewater (not shown) to the input section 2025. As for other embodiments of the present disclosure, the source of wastewater for the UV disinfection unit 2000 may include the output of a residential or multi-dwelling wastewater treatment system that separates solids from liquids and partially treats the liquid portion of the wastewater using rotating biological contactors. In other embodiments, the UV disinfection unit 2000 can be used to disinfect water suitable for human consumption.

The wastewater enters the wastewater inlet section 2001 at the opening 2002, flows downwards through the wastewater inlet section 2001, enters the treatment chamber 2022 at the input section 2025 and flows upwardly through the treatment chamber 2022, out of the output section 2027, towards the connector (or connection assembly) 2024 and out of the wastewater outlet 2030, which is part of the connector assembly 2024. The connector assembly 2024 connects the output section 2027 of the treatment chamber 2022 to the outside of the wastewater outlet 2040. The arrows 2032 in FIG. 12 indicate the direction of wastewater flow in the wastewater disinfection unit 2000.

An air inlet conduit 2036 allows for an air source (not shown) or, more generally, a gas source, to be connected to the treatment chamber 2022 to periodically inject air into the treatment chamber 22. The air inlet conduit 36 can be connected with any suitable type of piping or tubing to an air source or gas source (for example an air pump of a source of compressed air or another compressed gas). Some embodiments can operate with a liquid fluid (e.g., clean water) being injected rather than a gas. In such embodiments, the direction in which the liquid fluid is being injected is generally upwardly such as to provide an impulse to the pieces of media in order to cause the pieces of media to move along the length of the treatment chamber 2022 and to clean components against which they rub. The pressure range at which the liquid fluid can be injected in order to produce the cleaning effect in a given treatment chamber can be determined by routine testing performed by a skilled worker.

The remainder of the components of the UV disinfection unit 2000 are the same as those shown in the embodiments presented at FIGS. 1 through 7.

Figure 13:
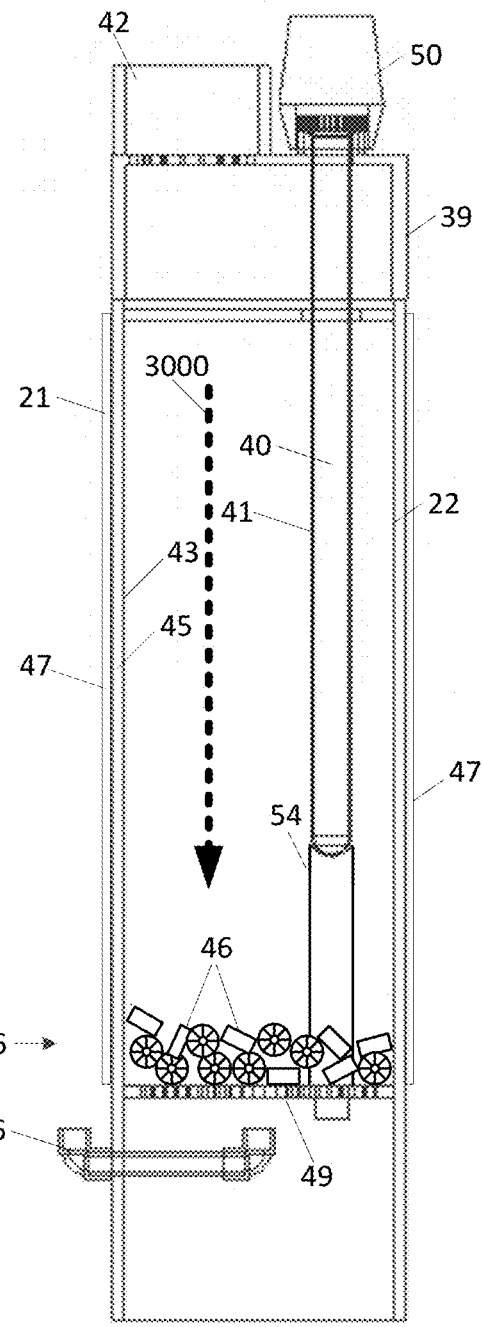
FIG. 13 shows a see-through, side view of the treatment chamber of the UV disinfection unit of FIG. 1, with pieces of media resting at the bottom section of the treatment chamber.

In embodiments where the wastewater traverses the treatment chamber from top to bottom (e.g., the embodiment shown at FIG. 1), the pieces of media present in the treatment chamber rest at the bottom region of the treatment chamber when the air source is off. This is shown at FIG. 13 where the pieces of media 46 are at the bottom section of the treatment chamber 22, on the strainer 49, and where the direction of the wastewater flow is indicated by arrow 3000.

Figure 14:
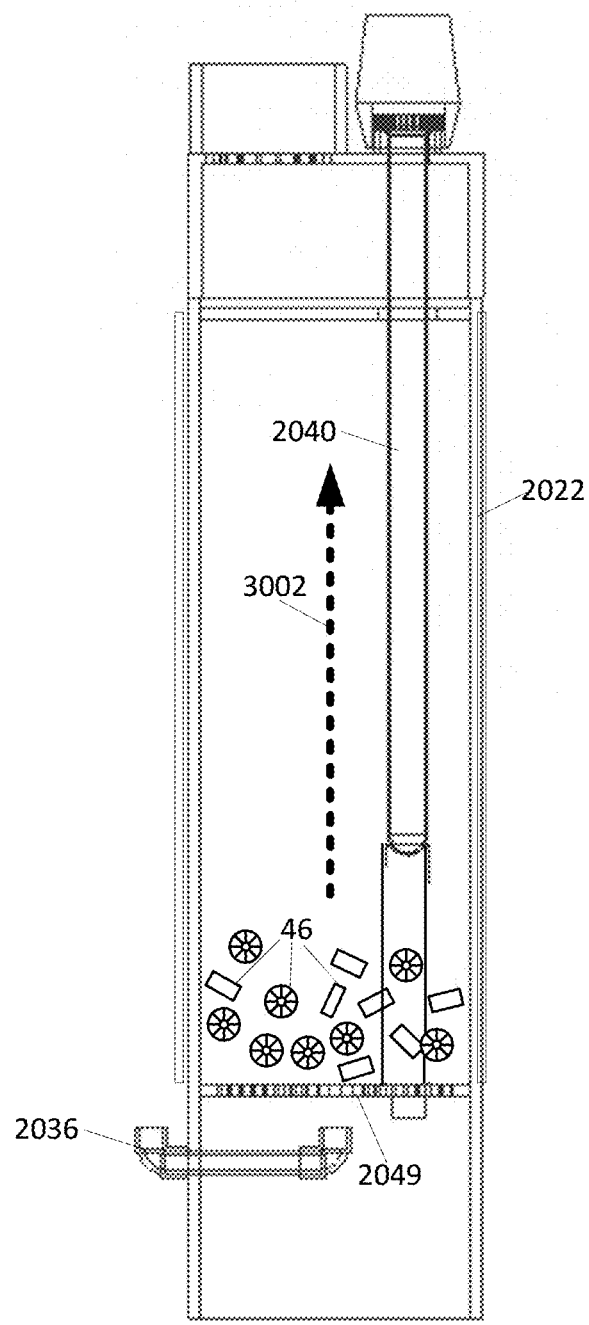
FIG. 14 shows a see-through, side view of the treatment chamber of the UV disinfection unit of FIG. 12, with pieces of media suspended above the strainer of the treatment chamber.

In the embodiments where the wastewater traverses the treatment chamber from bottom to top (e.g., the embodiment shown at FIG. 12), the pieces of media present in the treatment chamber are subjected to an upward flow of the wastewater. The inventor has discovered that, in these embodiments, operating the UV disinfection unit at a predetermined wastewater current speed causes the pieces of media to remain suspended and moving in the bottom region of the treatment chamber when the air source is off. This is shown at FIG. 14 where the pieces of media 46 are suspended at the bottom section of the treatment chamber 2022, above the strainer 2049, and where the direction of the wastewater flow is indicated by arrow 3002. This behavior of the pieces of media in the treatment chamber can be obtain for many different combinations wastewater current, density of the pieces of media and dimensions of the treatment chamber. As an example, for a typical filing ratio of the treatment chamber with the pieces of media (discussed above) a wastewater current of 2.5 to 5.0 litres per minute, a media density of 1.15 g/cm$^3$, and a cylindrical treatment chamber having a diameter of four 4 inches result in the pieces of media being suspended at the bottom section of the treatment chamber, above the strainer 204, as shown at FIG. 14. As will be understood by the skilled worker, for the same wastewater current, having a treatment chamber diameter smaller than 4 inches would cause the wastewater to move at greater speed through the treatment chamber and the pieces of media to rise higher. And, for the same wastewater current, having a treatment chamber diameter greater than 4 inches would cause the wastewater to move at lower speed through the treatment chamber and the pieces of media to not rise as high.

By remaining suspended in the bottom region, the pieces of media 46 do not substantially block UV light generated by the UV light unit 2040 or prevent the UV light from disinfecting the wastewater.

Figure 15:
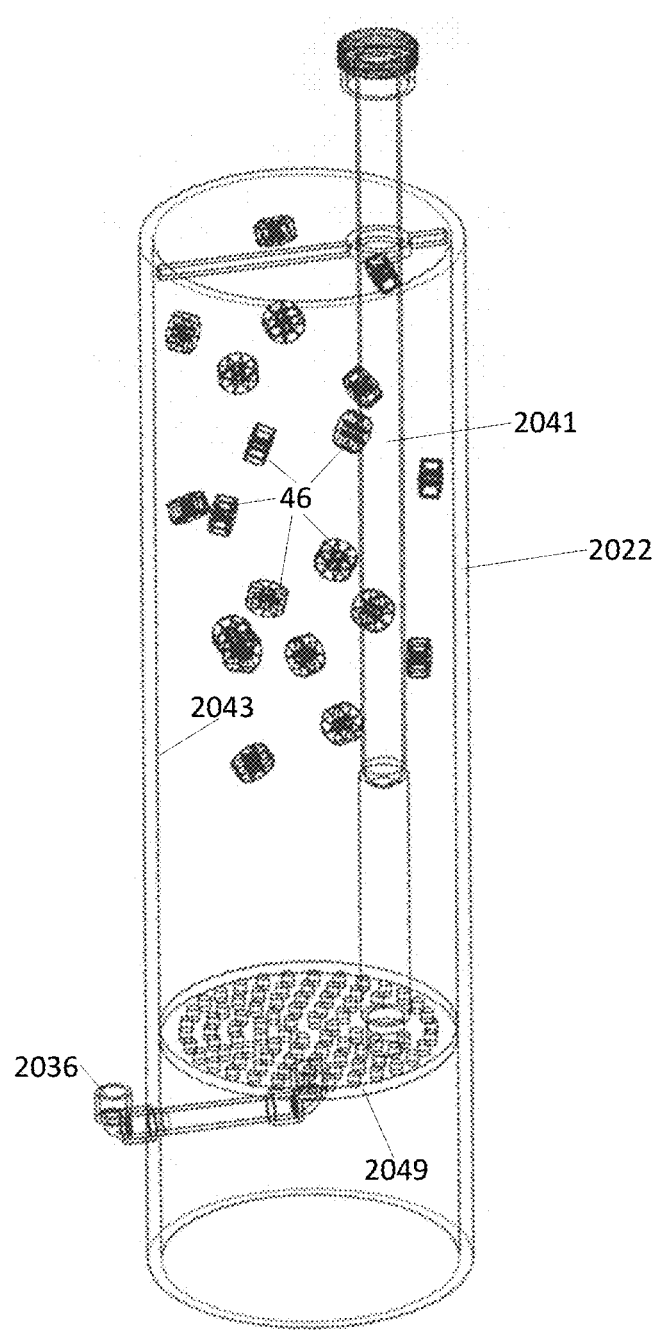
FIG. 15 shows a see-through, perspective view of the treatment chamber of the UV disinfection unit of FIG. 12, with pieces of media moving through the treatment chamber under the influence of a gas provided at the bottom section of the treatment chamber.

When air is provided to the air inlet input 46, the pieces of media 46 move along the whole length of the treatment chamber 2022, as shown in FIG. 15, and rub against the lamp sleeve 2041 as well as against the surface of other components of the disinfection unit within the treatment chamber 2022, including the inner wall surface 2043 of chamber 22. The brushing or rubbing movement of the pieces of media against the surfaces of components within the treatment chamber 2022 has a cleaning effect on these surfaces. For example, the rubbing may mitigate the accumulation of a biofilm or other matter on the surfaces within the chamber. The turbulence in the wastewater created by air flowing in the wastewater may also mitigate the accumulation of such biofilms or other matter. This may allow for prolonged use of the disinfection unit without the need for a significant cleaning of the treatment chamber and its components at short time intervals.

In the embodiment of FIGS. 1 and 2, the wastewater inlet 30 is positioned higher than the wastewater outlet 34. However, this need not be the case. For example, the wastewater inlet 30 and the wastewater outlet 34 can be at the same height, such as shown in the embodiment of FIG. 12 where the wastewater inlet 2002 is at the same height as the wastewater outlet 2030. In other embodiments, the wastewater inlet 2002 can be higher or lower than the wastewater outlet 2032.

Whatever the height of the wastewater inlet 2002 may be with respect to the height of the wastewater outlet 2032, the treatment chamber should preferably always contain wastewater or disinfected water. This is to prevent the formation of stains on the UV lamp sleeve due do drying in the treatment chamber and to prevent overheating of the UV lamp (the water present in the treatment chamber dissipates heat from the UV lamp). As an example, supposing the wastewater supply can occasionally be cut off, the UV disinfection unit 2000 should be preferably configured such that the wastewater inlet 2002 is no lower than the output section 2027 of the treatment chamber 2022. In the embodiment of FIG. 2, for the same reasons (i.e. to prevent staining), the UV disinfection unit 20 should be preferably configured such that the wastewater outlet section 34 is no lower than the input section 24 of the treatment chamber 22.

The structure, features, accessories, and alternatives of embodiments described herein and shown in the Figures are intended to apply generally to all of the teachings of the present disclosure, including to all of the embodiments described and illustrated herein, insofar as they are compatible. In other words, the structure, features, accessories, and alternatives of a specific embodiment are not intended to be limited to only that specific embodiment unless so indicated.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A disinfection unit to disinfect water, the water being drinking water or wastewater, the disinfection unit comprising:
   a treatment chamber to receive the water, the treatment chamber having a length, a top portion and a bottom portion;
   an ultraviolet (UV) lamp unit located within the treatment chamber, the UV lamp unit having a UV lamp and a sleeve portion, the UV lamp configured to generate UV light, the sleeve portion configured to transmit UV light generated by the UV lamp, the sleeve portion having a length shorter than the length of the treatment chamber;
   an inlet configured to provide the water to the treatment chamber;
   an outlet configured to output, from the treatment chamber, disinfected water, the inlet and the outlet being positioned at a height above the UV lamp unit, the inlet and the outlet being configured to provide the water flowing from the bottom portion of the treatment chamber toward the top portion of the treatment chamber;
   a gas inlet conduit in fluid communication with the treatment chamber and configured to inject gas in the treatment chamber from a position that is below the sleeve portion; and
   pieces of media positioned in the treatment chamber;
   wherein:
   when water is present in the treatment chamber and flowing, at a pre-determined current, from the bottom portion of the treatment chamber toward the top portion of the treatment chamber, the pieces of media are configured to float below the sleeve portion when gas is not injected into the water through the gas inlet conduit, and
   when water is present in the treatment chamber and flowing, at the pre-determined current, from the bottom portion of the treatment chamber toward the top portion of the treatment chamber, the pieces of media are configured to become agitated and rub against the sleeve portion to remove matter accumulated on the sleeve portion, when the gas is injected into the water through the gas inlet conduit.

2. The disinfection unit of claim 1, wherein the density of the pieces of media is within the range of approximately 1.05 to 1.15 g/cm$^3$.

3. The disinfection unit of claim 1, wherein the pieces of media consist substantially of plastic.

4. The disinfection unit of claim 1, comprising at least two gas inlet conduits in fluid communication with the treatment chamber, wherein the gas inlet conduits are oriented within the treatment chamber to induce a vortex effect in the water when gas is injected into the water through the gas inlet conduits.

5. The disinfection unit of claim 1, wherein the gas inlet conduit is positioned below the pieces of media.

6. The disinfection unit of claim 1, further comprising:
an input section for receiving the water into the treatment chamber; and
a filter for preventing pieces of media from exiting the treatment chamber through the input section.

7. The disinfection unit of claim 1, further comprising a gas exhaust conduit in fluid communication with the treatment chamber for allowing gas to leave the treatment chamber as gas is injected into the water through the gas inlet conduit.

8. The disinfection unit of claim 7, further comprising:
an exhaust valve positioned along the gas exhaust conduit that may be selectively closed when no gas is to be injected into the water through the gas inlet conduit to prevent the flow of water from the treatment chamber through the gas exhaust conduit.

9. The disinfection unit of claim 1, further comprising:
a water supply conduit for receiving the water into the treatment chamber; and
a supply valve positioned along the water supply conduit that may be selectively closed when gas is going to be injected into the wastewater to prevent backflow of water or gas from the treatment chamber into the water supply conduit.

10. The water disinfection unit of claim 1, further comprising a dosing mechanism in fluid communication with the treatment chamber for selectively providing a dose of cleaning substance into the treatment chamber.

11. A method of removing matter accumulated on a surface of a ultraviolet (UV) lamp unit located within a treatment chamber of a water disinfection unit, the method comprising:
providing pieces of media within the treatment chamber, the pieces of media having a density higher than that of water;
providing water within the treatment chamber to effect, by gravity, a flow of water from a bottom portion of the treatment chamber toward a top portion of the treatment chamber;
wherein:
the water is drinking water or wastewater;
the treatment chamber has a length;
the UV lamp unit has a UV lamp and a sleeve portion, the UV lamp is configured to generate UV light, the sleeve portion is configured to transmit UV light generated by the UV lamp, and the sleeve portion has a length shorter than the length of the treatment chamber;
and
starting from a state where water is present in the treatment chamber and flowing, at a pre-determined current, from the bottom portion of the treatment chamber toward the top portion of the treatment chamber, with the pieces of media floating below the sleeve portion and without gas being infected into the water through the gas inlet conduit, injecting the gas into the water in the treatment chamber to agitate the pieces of media in the water to cause the pieces of media to rise in the treatment chamber and to rub against the sleeve portion to remove the accumulated matter from the sleeve portion.

12. The method of claim 11, wherein injecting gas into the water involves directing gas within the water to induce a vortex effect in the wastewater.

13. The method of claim 11, comprising injecting gas into the water from at least two different locations within the treatment chamber.

14. The method of claim 11, further comprising selectively opening an exhaust valve positioned along a gas exhaust conduit in fluid communication with the treatment chamber to exhaust gas from the treatment chamber during the injecting gas into the wastewater.

15. The method of claim 11, further comprising selectively closing a supply valve positioned along a water supply conduit in fluid communication with the treatment chamber to prevent backflow of water or gas from the treatment chamber into the water supply conduit.

16. The method of claim 11, further comprising selectively providing a dose of cleaning substance into the treatment chamber.

17. The disinfection unit of claim 5, further comprising a strainer positioned below the sleeve portion, wherein:
when water is present in the treatment chamber and flowing, at a pre-determined current, from the bottom portion of the treatment chamber toward the top portion of the treatment chamber, the pieces of media are configured to float above the strainer and below the sleeve portion when gas is not injected into the wastewater through the gas inlet conduit.

* * * * *

UNITED STATES PATENT AND TRADEMARK OFFICE
CERTIFICATE OF CORRECTION

PATENT NO. : 10,597,311 B2
APPLICATION NO. : 15/599922
DATED : March 24, 2020
INVENTOR(S) : Paul Mayrand Page 1 of 1

It is certified that error appears in the above-identified patent and that said Letters Patent is hereby corrected as shown below:

In the Claims

In Column 13, Line 42-43: delete "accumulated on a surface of a ultraviolet (UV) lamp unit" and replace with "accumulated on an ultraviolet (UV) lamp unit".

In Column 14, Line 16: delete "infected" and replace with "injected".

Signed and Sealed this
Seventh Day of July, 2020

Andrei Iancu
*Director of the United States Patent and Trademark Office*